United States Patent [19]

Jeutter

[11] Patent Number: 5,314,453
[45] Date of Patent: May 24, 1994

[54] POSITION SENSITIVE POWER TRANSFER ANTENNA

[75] Inventor: Dean C. Jeutter, Grafton, Wis.

[73] Assignee: Spinal Cord Society, Fergus Falls, Minn.

[21] Appl. No.: 803,022

[22] Filed: Dec. 6, 1991

[51] Int. Cl.⁵ .............................................. A61N 1/08
[52] U.S. Cl. ........................................ 607/61; 607/60
[58] Field of Search ....... 128/419 R, 419 PS, 419 PT, 128/899, 421, 903; 600/12, 13; 607/30, 31, 32, 33, 60, 61, 2

[56] References Cited

U.S. PATENT DOCUMENTS

| Re. 32,947 | 6/1989 | Dormer et al. | 600/13 |
|---|---|---|---|
| 3,195,540 | 7/1965 | Waller | 607/33 |
| 4,679,560 | 7/1987 | Galbraith | 128/419 R |
| 4,726,378 | 2/1988 | Kaplan | 128/419 R |

Primary Examiner—William E. Kamm
Assistant Examiner—Kennedy J. Schaetzle
Attorney, Agent, or Firm—Palmatier, Sjoquist & Helget

[57] ABSTRACT

A power supply implanted behind a tissue barrier in a human body and operating a medical device and incorporating a high frequency power receiver antenna coil; a transmitter having a high frequency transmitter antenna coil generating high frequency power and transmitting the power from the transmitting coil to the implanted receiver coil; an implanted non-ferrous magnet affixed within the implanted annular receiver coil; and a magnetic field sensing device or magnetically operated reed switch affixed concentrically within the transmitter coil of the transmitter and controlling transmission of high frequency power from the transmitter to the implanted power supply.

18 Claims, 6 Drawing Sheets

POSITION SENSITIVE POWER TRANSFER ANTENNA

This invention relates to transmission of high frequency energy from a transmitting antenna coil to a receiving coil implanted in a person's body, and more particularly, to a device for indicating proper physical positioning between such coils for full power transfer.

BACKGROUND OF THE INVENTION

Various types of medical devices may be implanted in a person's body to assist normal body functions or to provide therapeutic functions. One example is a nerve stimulator which may be implanted for therapeutic purposes to act on the nerves in a person's body.

Such an implanted device may need to be supplied with power from outside the body for recharging batteries or for operating the device. Similarly, some devices require data transfer by telemetry. High frequency transfer to the implanted device requires an implanted receiving coil receiving high frequency power from a transmitter antenna coil at the outside of the body. Of course, the transmitter coil and receiver coil must be properly positioned relative to each other as to be coupled with each other for maximum transfer of high frequency power Proper position may be difficult when the precise location of the implanted receiver coil is not known.

High frequency power may be transmitted at approximately 2 MHz (VHF) or at 70 MHz (VHF) or more.

SUMMARY OF THE INVENTION

An object of the invention is to provide for the maximum transfer of high frequency power between high frequency transmitting and receiving coils where the receiving coil is implanted with a device behind a non-electrically conductive barrier, and wherein such a device is a medical device implanted in a person's body.

A feature of the invention is a device to indicate the alignment, as distinguished from misalignment in any of three directions, i.e., axial, lateral and angular directions, between a transmitter antenna coil and receiving coils wherein the transmitter coil is implanted behind a non-electrically conductive barrier such as a tissue barrier of a person's body.

Another feature of the invention is an aligning device utilizing a non-ferrous magnet and a magnetic field sensing device respectively concentrically arranged in the high frequency transmitter antenna and receiver coils as to produce an indication when the coils are properly aligned and coupled for nearly maximum high frequency power transfer between the coils separated by a tissue barrier. By using the non-ferrous magnet, eddy currents are eliminated or minimized as to prevent interference with the high frequency transfer of power. In the preferred form, the sensing device comprises a magnetically operated reed switch opening when the field from the magnet is remote or misaligned to prevent transmissions of high frequency power by the transmitter antenna coil.

Still another feature is the method of aligning high frequency transmitter antenna and receiving coils wherein one of the coils is implanted behind a tissue barrier, by establishing a magnetic field emanating from one of the coils and sensing the field adjacent the other coil as to produce an indication of the relative positions of the coils so that alignment and coupling of the coils can be assured.

DETAILED SPECIFICATION

A preferred form of the invention is illustrated in FIGS. 1-7.

Figure 1:
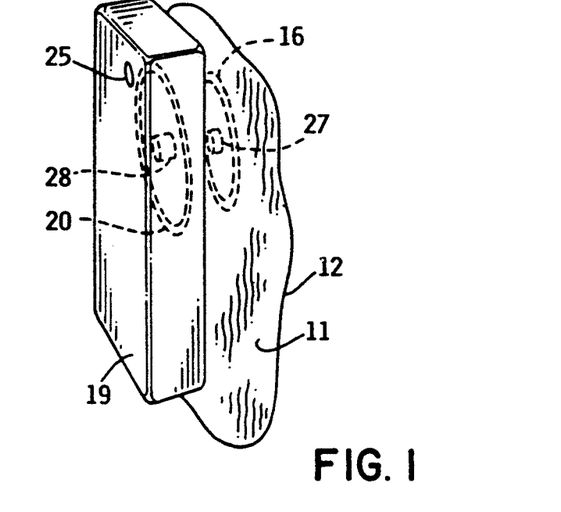
FIG. 1 is a diagrammatic detail view illustrating the power transmitter and the receiver antenna coil embedded behind a tissue barrier of an illustrated detail portion of a human body.
Figure 2:
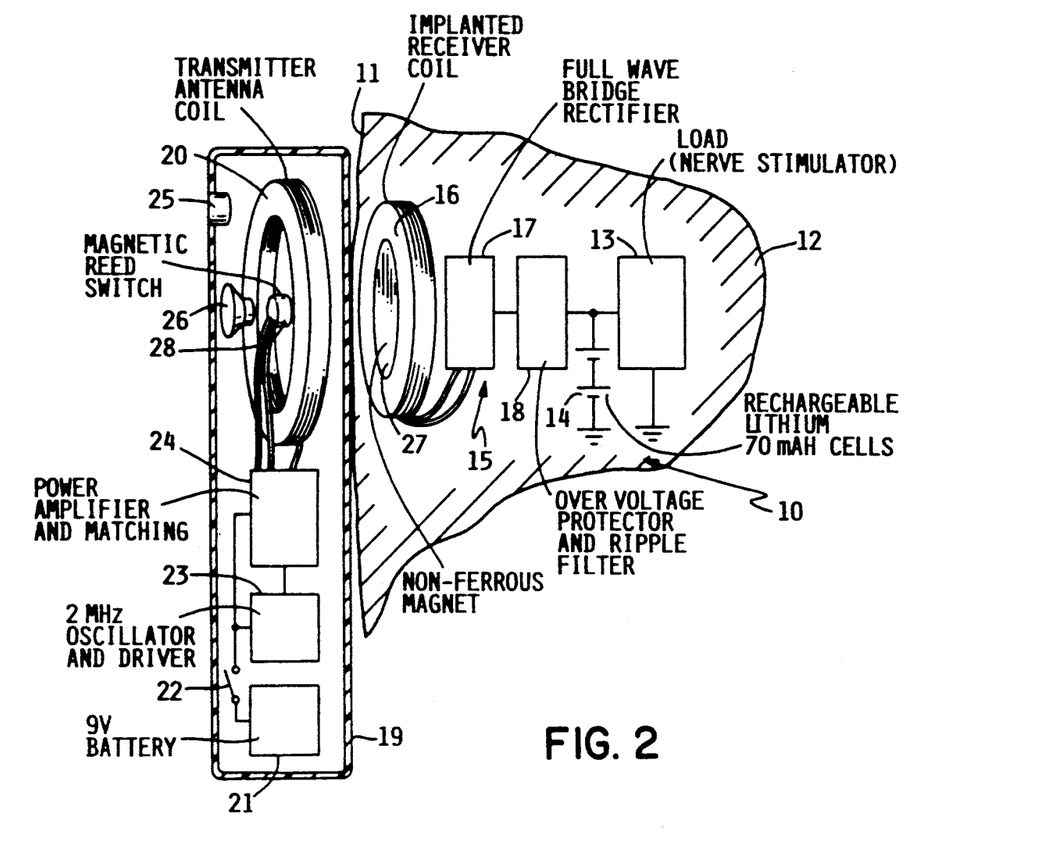
FIG. 2 is a diagrammatic block diagram illustrating the present invention.

FIGS. 1 and 2 illustrate the principal aspects of the present invention wherein a medical device indicated in general by numeral 10 is implanted behind a tissue barrier 11 within the body 12 of a person. Although the active portion of the medical device 10 may take varying forms, a typical active portion of the medical device 10 may be a nerve stimulator.

A rechargeable power source in the form of two rechargeable batteries 14 supply power to the medical device 13. Without recharging capability, the medical device 14 has only a very limited service life after implantation. Recharging power is supplied by a power receiver, indicated in general by numeral 15 and including a high frequency receiver coil 16 implanted immediately adjacent the tissue barrier 11 and connected to a full wave bridge rectifier 17 which is connected through an over voltage protector and ripple filter 18 to the rechargeable lithium batteries 14.

The output voltage from the rechargeable batteries 14 to the medical device 13 is approximately 6 volts DC.

Power is supplied to the implanted power supply and coil 16 by a transmitter, indicated in general by numeral 19 from which high frequency energy is transmitted from a high frequency transmitter antenna coil to the implanted coil 16, when the two coils are properly positioned with respect to each other and in alignment. The transmitter is illustrated in block diagram in FIG. 2 and is shown in more detail in FIG. 3. In FIG. 2, it will be recognized that the transmitter 19 utilizes a 9 volt battery 21 connected through an on/off switch 22 to an oscillator and driver 23 which generates the high frequency signal which is amplified in the power amplifier block 24 and then transmitted to the coil 20 from which high frequency power is transmitted through the tissue barrier 11 to the implanted receiver coil 16.

The transmitter 19 also includes an indicator light 24 as to indicate when the coil 20 is aligned with the implanted coil 16 so that nearly maximum power is transmitted to the coil 16.

Further, a beeper or buzzer 26 is incorporated into the transmitter to sound when, during a charging session, a misalignment occurs between the two coils 20 and 16.

It is to be noted that the oscillator 23, power amplifier 24, and transmitter antenna coil 20 operate satisfactorily at an operating frequency (VHF) of 2 MHz. It has been determined that operating at frequencies of 70 MHz (UHF) prove to be satisfactory as well. It is believed that using microwave frequencies above 300 MHz should be satisfactory as well.

Figures 5, 7:
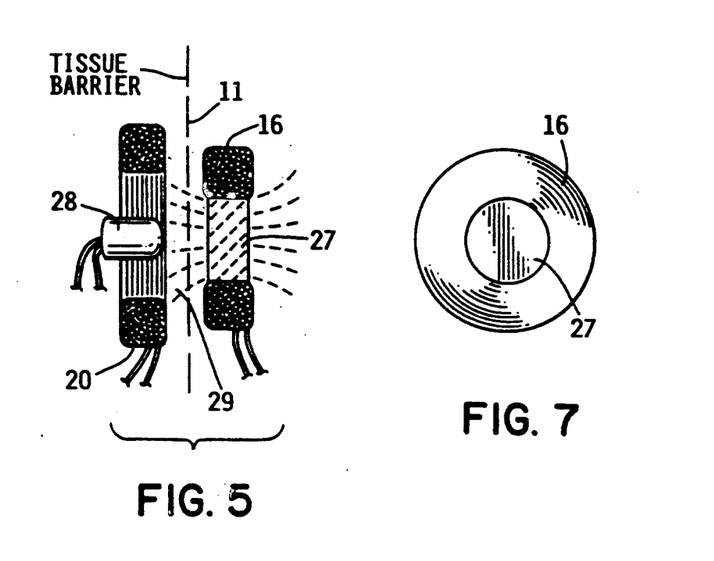
FIG. 5 is a cross section view of the two transmitter and receiver coils located on opposite sides of the tissue barrier and also diagrammatically illustrating the non-ferrous magnet and the magnetic reed switch located in opposite coils.
FIG. 7 is an elevation view of the receiver coil.

According to the present invention, the transmitter antenna coil 20 can be properly aligned with the implanted coil 16 through the use of a permanent non-ferrous magnet 27 affixed concentrically within the implanted receiver coil 16 and implanted therewith; and a magnetically responsive reed switch 28 affixed concentrically within the transmitter antenna coil 20. When the magnet 27 is aligned with the reed switch 28, the two coils 16 and 20 are also aligned for nearly maximum transmission of high frequency power.

The magnet 27 serves as a disseminating portion exuding a sensible media, i.e., the non-varying magnetic field indicated by the numeral 29, which is capable of passing through the tissue barrier 11 and is distinguishable from the high frequency signals being transmitted between the coils.

The magnetically operated reed switch 28 acts as a sensing portion detecting the sensible medium, i.e., the magnetic field 29, for determining when the reed switch is aligned axially laterally and angularly with the center of the magnetic field 29 and the magnet 27 and therefore when the coil 20 is aligned with the coil 16.

Figure 6:
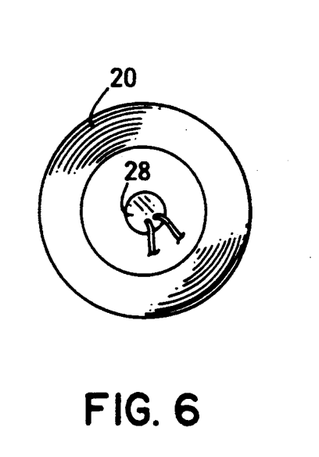
FIG. 6 is an elevation view of the transmitter coil.

It will be recognized that the transmitter coil 20 is slightly larger than the implanted receiver coil 16. In use, it has been found satisfactory that the transmitting antenna coil 20 is 1.25 inch diameter; and the implanted receiver coil 16 is slightly smaller at one inch in diameter. Both of the coils 20 and 16 are annular in shape.

The magnet 27 is a ceramic Grade V magnet, 15/32 inch in diamater, and 5/32 inch thick. The magnet was chosen both for its magnetic strength and its size which permits it to be positioned concentrically within the annular receiver antenna coil 16 which is ⅛ inch long. The magnet 27 is made of oriented ceramic with an energy product of 3.5 million Gauss-Oersted. It will also be recognized that the flat face of the magnet 27 defines a pole face immediately adjacent the tissue barrier and that the magnet field exuding from the magnet has directionality and is also concentric with the center line of the circular magnet 27 which fits into the interior of the annular coil 16.

It is important to recognize that because the magnet 27 is a ceramic magnet and a non-ferrous magnet, this form of magnet minimizes the effects of having an activating device located concentrically within the power transfer region of the antenna coils 16 and 20. Furthermore, the use of a non-ferrous magnet minimizes any eddy current losses and antenna coil inductance changes. It has been determined that in transferring power at high operating frequencies of 2 MHz, there is no measurable change in the power transfer performance between the coils when the magnet is introduced into the power transfer region.

The reed switch 28 is also located at the center and concentrically of the annular transmitter coil 20 and is affixed in that location. The reed switch is a magnetically operated switch and is normally open. When this miniature switch is within its operating region of the implanted magnet, the switch 28 is closed, and moves to an open position unambiguously when the switch moves beyond its "drop out" (DO) range. The reed switch 28 has a drop out threshold of 4 to 8 Gauss and a "pull up" (PU) threshold of about 4 Gauss. The particular switch used was obtained from Hermetic Switch, Inc. and is designated Part No. HSR-004DT. Of course, reed switches of different sizes and different DO/PU characteristics can be used to shape the position response between the transmitter and receiver coils. Moreover, active magnetic sensors such as Hall Effect switches could be used as the external sensor.

The implanted coil 16 is resonant at 2 MHz and is implanted along with the other circuitry designated in the block diagrammed FIG. 2 in a potted medical grade epoxy and covered with a thin medical grade silicone rubber skin.

The transmitter antenna coil 20 and the reed switch 28 may be cast in fixed relation to each other and into medical grade silicone rubber and attached to the subject's (patient's) skin with removable double adhesive tape (Tegaderm) transparent I.V. dressing material manufactured by 3M Company of St. Paul, Minnesota.

Figure 3A:
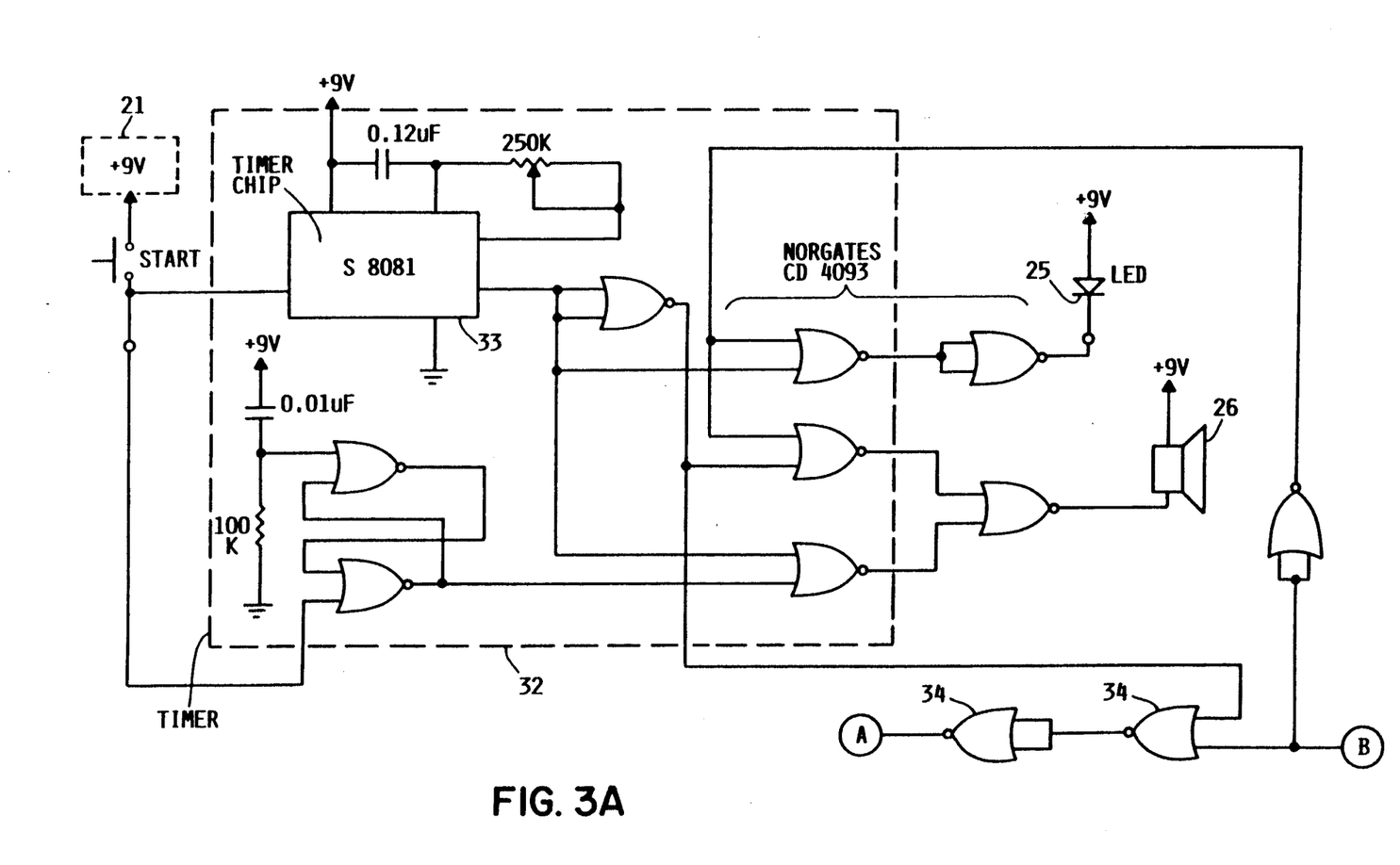
FIGS. 3A, 3B and 3C are circuit diagrams cumulatively presenting the schematic circuit diagram of the power transmitter, and the segments of the circuit diagram presented in the separate views are joined together at the letters A, B and C which are common to the several circuits in FIGS. 3A, 3B and 3C.
Figure 3B:
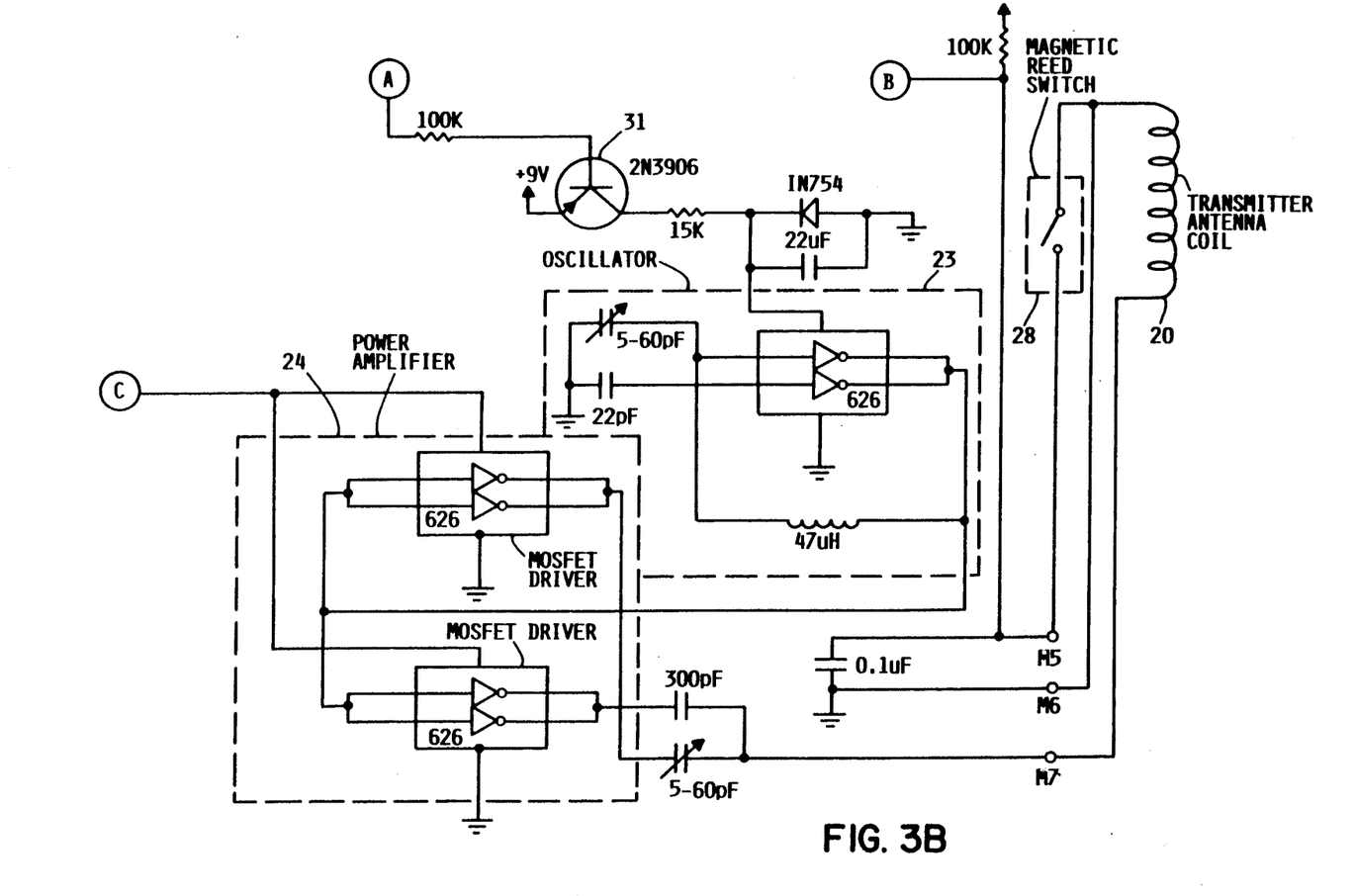
Figure 3C:
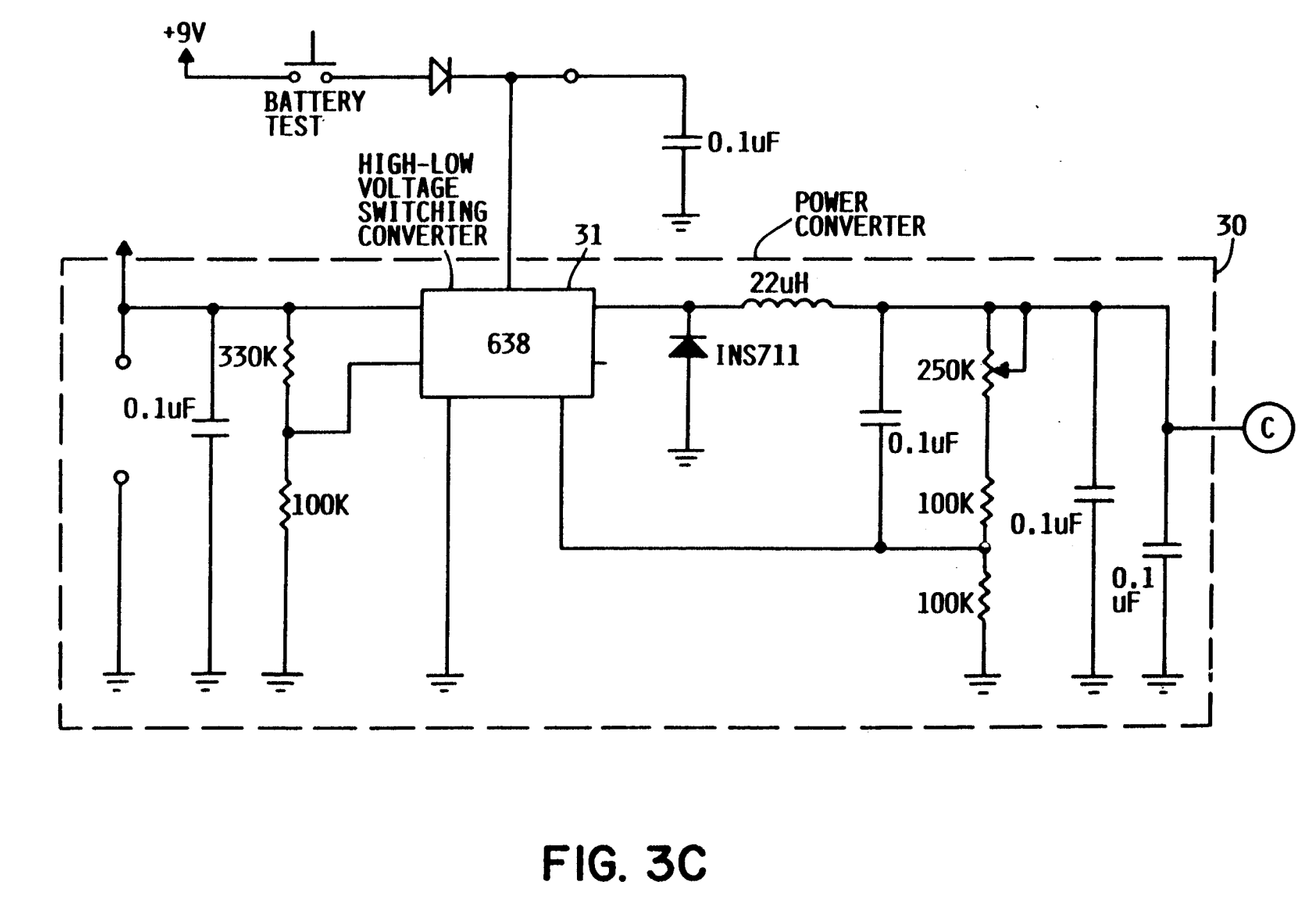
Figure 4:
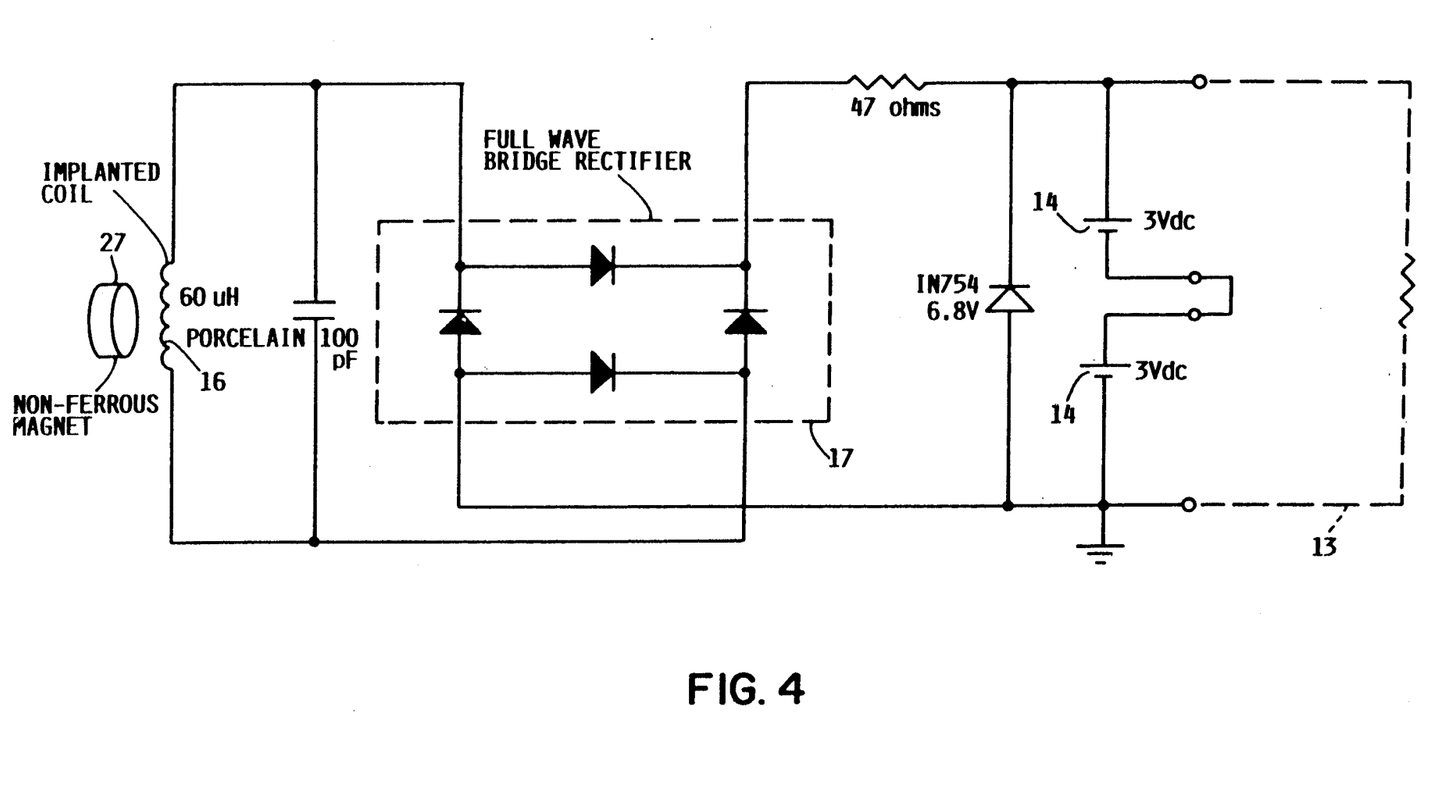
FIG. 4 is a schematic diagram of the implanted receiver to which high frequency power is transmitted.

The circuit diagrams of FIG. 3 and FIG. 4 are self evident.

In FIG. 4, all of the implanted circuitry and magnet 27 are illustrated. The full wave rectifier 17 is seen, along with the rechargeable batteries, Sanyo No. ML2430, 3 volts DC. The medical device is indicated in general by the numeral 13.

In FIGS. 3A, 3B and 3C, which are connected into a single circuit at the letters A, B and C, the high frequency transmitting antenna coil 20 is seen, together with the adjacent magnetically operated reed switch 28. The entire circuitry of FIG. 3 is powered from a 9 volt battery.

The power converter is indicated by numeral 30 and incorporates a high/low voltage switching converter 31. The output from the power converter 30 is directed into the power amplifier 40 which utilizes two Mosfet drivers. The high frequency oscillator is indicated by the numeral 23 and is controlled by a switching diode 2N3906, identified by numeral 31.

A timing circuit 32 incorporates a timer chip 33 which is identified as an S-8081 timer chip. The timing circuit incorporates a number of norgates, CD-4093, certain of which operate the LED 25 to indicate the aligned condition between antenna coils 20 and 16; and the beeper or buzzer 26 operable when, during a charging session, a misalignment should occur.

A pair of Norgates, indicated by numeral 34, are operated either by expiration of time of the timing circuit, or by closing of the reed switch 28 to operate the switching diode 31 as to prevent operation of the oscillator when the switch 28 is open or the timer has expired so that high frequency power is no longer transmitted to the transmitting antenna coil 20.

During use of the transmitter 19 in charging the rechargeable batteries 14, or in supplying power directly into the medical device 13, the transmitter is placed or laid against the skin so that the coils 20 and 16 are substantially aligned. When the magnetically operated reed switch senses the field of the non-ferrous magnet 27 at or above the PU threshold, the switch 28 is closed, causing the oscillator to be started, the output from which is supplied through the power amplifier to the transmitter antenna coil 20, causing power transfer to receiver coil 16 and charging of the batteries 14. Simultaneously with starting the oscillator, the LED 25 is illuminated so as to produce a visual indication on the transmitter 19 that the alignment between the two antenna coils 16 and 20 is proper for nearly maximum transmission of high frequency power. In the event that the transmitter 19 and switch 28 move beyond the drop out range of the switch 28 in relation to the field of magnet 27, the switch 28 will open and will cause the diode 31 to de-energize the oscillator so that no output will thereafter be transmitted from the coil 20. When the reed switch 28 is opened, the LED 25 is darkened and the beeper 26 is sounded so as to draw the attention of an operator or attendant to readjust the transmitter and again properly position it in alignment with the implanted antenna receiver coil 16.

Misalignment is detected by the reed switch in a number of ways. Misalignment of the reed switch and transmitter coil 20 away from the implanted coil 16 and magnet 27 may be caused by the transmitter moving laterally to one side, or the transmitter may be tilted to cause misalignment, or the transmitter may be simply left in alignment by widely spaced relation with the magnet 27 and coil 16, whereupon the indicator light 25 will darken to indicate that the position of the transmitter is improper and the high frequency power will not be transmitted by the coil 20. When the transmitter is properly aligned with the implanted coil and the reed switch senses the magnetic field from magnet 27, the LED 25 will illuminate and the oscillator will again operate and high frequency power will be transmitted to the implanted coil and power supply.

Figure 8:
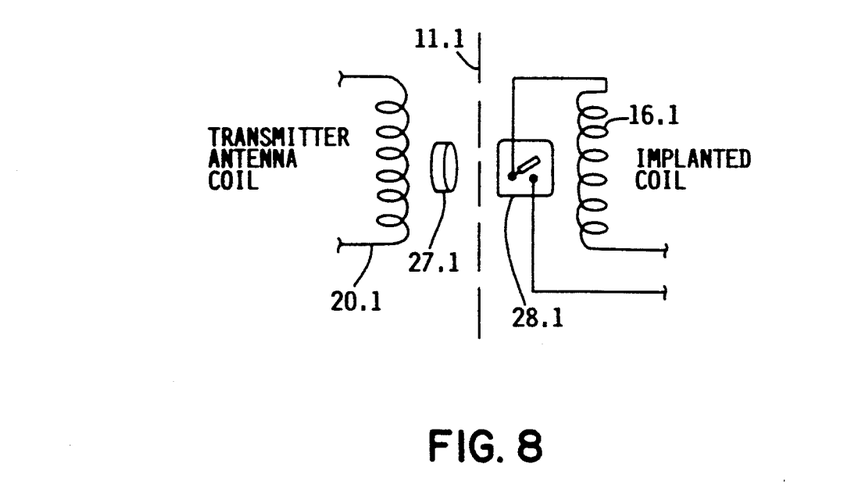
FIG. 8 is a diagrammatic view illustrating an alternate arrangement of the magnet and sensing device with the antenna and implanted coils.

It should be recognized that the position of the nonferrous magnet 27 and the reed switch may be interchanged, as illustrated in FIG. 8. In FIG. 8, the sensing device or magnetically operated reed switch 28.1 is implanted with coil 16.1 behind the tissue barrier 11.1. In one version of the circuit operation, the reed switch may be connected directly to the receiver coil 16.1 so that power is not transmitted in the event the reed switch and the magnet 27.1 are misaligned. The transmitting coil 20.1 will have the non-ferrous magnet 27.1 affixed concentrically within the annular coil 20.1 so that when the sensing device 28.1 senses the presence of a magnetic field from magnet 27.1, it will be known and it will be indicated that the alignment is proper and transmission of high frequency power will be commenced and continued.

An important aspect of the present invention is the method of nearly maximizing high frequency signal transmissions between a high frequency receiver coil which is implanted behind a tissue barrier, as in a human body, and a high frequency transmitter antenna coil which may be variably placed adjacent the tissue or on the skin of the person's body and adjacent the receiver coil. As a part of the method, a disseminating portion, i.e., the permanent magnet 27, is placed adjacent one of the coils and preferably the implanted coil, so as to be in a predetermined fixed relation with the coil so that the disseminating portion or magnet 27 exudes a sensible media, i.e., the magnetic field, which is capable of passing through the tissue barrier and which is capable of being distinguished from the high frequency power being transmitted. Another part of the important method is the placing of a sensing portion, i.e. the magnetic reed switch, responsive to the magnetic field of the magnet 27, and in predetermined fixed relation with the other of the coils. Preferably, the sensing portion or reed switch is placed concentrically within the transmitter coil which is outside the body so that the sensing portion or reed switch will sense the strength of the media or magnetic field exuded by the implanted magnet, and the sensing portion will control the transmission of the high frequency power in response to varying strengths of the frequency being passed through the tissue barrier. When the reed switch senses the field higher than the threshold of pull in level, the switch will close to cause the transmitter to operate, and when the reed switch and the transmitter coil are misaligned with the receiver coil and the magnet to the extent that the drop out threshold of the reed switch is passed, generation of high frequency power and transmission of such high frequency power will cease. The physical adjusting of the transmitter coil and the sensing portion associated therewith into alignment with the receiver coil and magnet will cause the high frequency power to again be transmitted from the transmitter coil to the receiver coil, and the indicator LED will indicate that the alignment is proper and that high frequency power is being transmitted.

It will be seen that I have provided a new and improved device for indicating and assuring the proper alignment of the transmitting and receiving antenna coils of a power transmitter and an implanted power supply by a non-ferrous magnet implanted with the receiver coil behind the tissue barrier of a human body; and a sensing device in the power transmitter sensing the magnetic field from the implanted magnet, which field can be and is readily distinguished from the power being transmitted by high frequency.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

I claim:

1. A high frequency transmitting and receiving device wherein a high frequency signal is generated by an external transmitter with a transmitter antenna coil, and the signal is transmitted between the transmitter antenna coil and a receiver coil wherein the receiver coil is implantable behind a tissue barrier, the device comprising:

a disseminating means adjacent the receiver coil for exuding a sensible media capable of passing through such a tissue barrier and distinguishable from the high frequency signal being transmitted;

and a sensing means adjacent the transmitter antenna coils for detecting said sensible media and for determining the proximity of the disseminating portion and therefore the relative proximity of the coils, the sensing means comprised of a switch means connected to the transmitter for alternately enabling and disabling the transmitter in correspondence to the relative proximity of the coils.

2. A high frequency transmitting and receiving device according to claim 1 wherein the sensible media comprises a magnetic field.

3. A high frequency transmitting and receiving device according to claim 2 wherein said magnetic field is a substantially non-varying field.

4. A high frequency transmitting and receiving device according to claim 1 wherein said disseminating portion comprises a non-ferrous magnet.

5. A high frequency transmitting and receiving device according to claim 1 wherein said disseminating means and said sensing means have fixed physical relationships with the respective coils.

6. A high frequency transmitting and receiving device according to claim 5 wherein the transmitter antenna coil and receiver coil are substantially annular in shape.

7. A high frequency transmitting and receiving device according to claim 6 wherein said disseminating and sensing means are located substantially concentrically of said coils.

8. A high frequency transmitting and receiving device according to claim 6 wherein the disseminating portion comprises a magnet with a pole face oriented to arrange the magnetic field substantially concentrically of the transmitting coil whereby the direction that the magnetic field is arranged varies corresponding to the orientation of the receiver coil.

9. A high frequency transmitting and receiving device according to claim 8 wherein said switch means is magnetically operated and is operationally responsive to alternate alignment and misalignment with the magnetic field, and wherein such misalignment maybe axial, lateral and angular.

10. A high frequency transmitting and receiving device wherein the switch means operates to disable the transmitter when misalignment is sensed and operates to enable the transmitter when alignment is sensed.

11. A high frequency transmitting and receiving device according to claim 10 further comprising an indicator means connected to the transmitter for indicating alternately when the transmitter is disabled and when it is enabled.

12. A high frequency transmitting and receiving device according to claim 6 wherein the disseminating portion comprises a non-ferrous magnet located concentrically within the receiver coil, the receiver coil and magnet implantable behind the tissue barrier.

13. A high frequency transmitting and receiving device according to claim 12 wherein the indicator means includes an audio signal when the transmitter is disabled and therefore when the coils are misaligned.

14. A radio frequency transmitting and receiving device comprising a power receiver implantable in a human body behind a tissue barrier for powering an implantable medical device, the power receiver comprising an implantable annular radio frequency receiver coil, said transmitting and receiving device also comprising a transmitter to be variably placed adjacent the tissue barrier and effecting a transmission of radio frequency power to the receiver coil, the transmitter comprising an annular radio frequency transmitter coil to be placed in alignment with the receiver coil, the improvement comprising a permanent non-ferrous magnet implantable with and fixed concentrically within the annular receiver coil, and comprising a magnetic field sensing means located concentrically within the annular receiver coil, and comprising a magnetic field sensing means located concentrically within the annular transmitter coil for responding to alternate alignment and misalignment with the magnet for indicating when proper position of the transmitter coil has been achieved, the sensing means including a switching means for enabling the transmitter when alignment is sensed and disabling the transmitter when misalignment is sensed.

15. A method of nearly maximizing high frequency signal transmission from a transmitter between high frequency receiver coil which is implanted behind a tissue barrier and a high frequency transmitter antenna coil connected to the transmitter and variably placed adjacent the tissue barrier, comprising:

implanting a disseminating portion adjacent the transmitter antenna coil and in a predetermined fixed relation with the transmitter antenna coil, the disseminating portion exuding a sensible media being capable of passing through the tissue barrier and being distinguishable from the high frequency power being transmitted, placing a sensing portion adjacent the receiver coil and in a predetermined fixed relation with the receiver coil, the sensing portion sensing the strength of said media and controlling the transmission of high frequency power in response to varying strengths of media passed thereto by enabling and disabling the transmitter, and physically adjusting the placement of said transmitter coil and the disseminating portion in fixed relation thereto relative to the receiver coil and the sensing portion until nearly maximum strength of media is sensed whereby the high frequency transmission between the coils is nearly maximized.

16. The method of claim 15 wherein said placing of the disseminating portion comprises implanting the disseminating portion with the implanted receiving coil.

17. The method claim 15 wherein said placing of the disseminating portion comprises a non-ferrous magnet.

18. The high frequency transmitting and receiving device according to claim 12 wherein the indicator means includes a light emitting diode to indicate when the transmitter is enabled and therefore when the coils are aligned.

* * * * *